United States Patent [19]

Vasilevsky et al.

[11] 4,192,294
[45] Mar. 11, 1980

[54] METHOD OF REMOVING CONCRETIONS FROM THE URETER

[76] Inventors: Petr N. Vasilevsky, bulvar Druzhby Narodov, 8, kv. 27; Boris S. Gekhman, ulitsa Parizhskoi kommuny, 22-b, kv. 24; Ivan V. Parfinenko, ulitsa Kochubeevskaya, 12a, kv. 1; Alfred M. Podgursky, pereulok Elektrotekhnichesky, 3, kv. 10; Avram S. Lazaretnik, Rusanovsky bulvar, 12, kv. 69, all of Kiev, U.S.S.R.

[21] Appl. No.: 840,763
[22] Filed: Oct. 11, 1977
[51] Int. Cl.² .................. A61B 19/00; A61B 17/00
[52] U.S. Cl. ................................. 128/1 R; 128/328
[58] Field of Search ................ 128/328, 24 A, 1 R

[56] References Cited

U.S. PATENT DOCUMENTS 3,735,764  5/1973  Balev et al. ...................... 128/328
3,861,391  1/1975  Antonevich et al. ............ 128/328

OTHER PUBLICATIONS

Physician's Desk Reference, 32 ed., 1978, pub. by Medical Economics Co., pp. 320, 1608, 1609, 1797, 1798.

Primary Examiner—Robert W. Michell
Assistant Examiner—C. W. Shedd
Attorney, Agent, or Firm—Steinberg and Blake

[57] ABSTRACT

A method is provided of removing urinary concretions from the ureter of patients whose anatomical peculiarities do not permit application of disintegrating instruments. The method involves an ultrasonic vibratory action upon the ureteral wall below the region where the concretion is lodged to stimulate peristaltic contractions of the urinary tract and free passage of the concretion. The local vibratory action upon the ureter involves no unfavorable effects upon the internal organs, cardiovascular or nervous systems of the patient.

10 Claims, 5 Drawing Figures

METHOD OF REMOVING CONCRETIONS FROM THE URETER

The present invention relates to urology, and more, particularly to methods of removing concretions from the ureter and can be used in internal treatment for urolithiasis.

Here and in what follows the term "concretion" applies to solid calculous formations of urates, oxalates and phosphates in the urinary tracts.

It is well known that bloodless removal of urinary concretions is a very urgent problem which has not been completely solved so far. In many cases, patients are hospitalized, and concretions are removed by means of a surgical operation. Attempts have been made to mechanically disintegrate concretions by ultrasonic vibrations without surgical intervention. However, these methods are impractical when such anatomical peculiarities as flexure of the ureter prevent the disintegrating instrument from being brought into contact with the concretion.

If concretions are relatively small (not more than 10 mm in cross-section), they may be removed from the ureter by means of loops or baskets which grip the concretions for mechanical extraction (cf. U.S. Pat. No. 3,074,408).

The use of such instruments, however, involves the danger of damaging the ureteral wall, in particular, at the moment of gripping the concretion, and is unsuitable when a flexure of the ureter or some other anatomical peculiarities of the patient prevent the disintegrating tool from being brought into contact with the concretion. In such cases, a method of internal treatment is used, according to which the patient is recommended to take large quantities of a liquid, such as water, to create excess pressure in the ureter over the concretion; at the same time, the organism of the patient is exposed to elevated temperatures, for instance by using hot baths.

Clinical experience has shown that this method produces positive results only in cases where the concretion is not larger than 3 mm. In addition, this method is contraindicated for patients suffering from cardiovascular diseases.

To solve the above problem, promising results have been attained by a method of removing concretions from the ureter, based on vibrotherapy. According to this method, the patient is put on a vibrobench and his organism is acted upon by vertical vibrations in the frequency range of 7 to 15 Hz, the amplitude being equal to 2 mm. The average duration of a continuous vibratory action is 30 minutes. After one or two seances of such treatment concretions as large as 5 to 6 mm in cross-section can be removed.

However, along with evident advantages, the above-described method has certain limitations, in particular, it has been found that this method is contraindicated for patients suffering from distinct atonia of the upper urinary tract, as well as from a number of other diseases, such as high arterial blood pressure (hypertension of the second and third degree), calculous cholecystitis, diseases of the peripheral nervous system in their aggravated stage, etc. In addition, the frequency range most efficient for this method closely approaches the alpha rhythm of the brain, and in certain cases may constitute a serious hazard to the patient, which is why the application of the above-described procedure of treatment is substantially limited.

It is an object of the present invention to provide a method of vibratory removal of concretions from the ureter, which excludes or minimizes the detrimental effect of vibration upon the internal organs and nervous system of the patient.

Another important object of the invention is to provide a method of vibratory removal of concretions, which has a wide field of application and can be used in the case of diseases which may become aggravated when the organism is exposed to vibration.

A further object of the invention is to enhance the efficiency of treatment for urolithiasis in cases where anatomical peculiarities do not permit a concretion to be fragmented in the ureter or mechanically extracted therefrom.

Still another object of the invention is to enable removal of concretions as large as 10 mm in size from the ureter.

Yet another object of the invention is to provide for a larger selection of methods of treatment for urolithiasis.

One more object of the invention is to minimize the danger of damaging the ureter and to improve the functional activity thereof.

A further object of the invention is to reduce the duration of vibratory action.

These and other objects of the invention are attained in a method of removing concretions from the ureter by exposing the organism to vibration wherein according to the invention, the vibration acts only upon the inner surface of the ureteral walls below the location of a concretion, thereby stimulating peristaltic contractions of the ureter.

The proposed method, as compared to the prior art, has the advantage of being applicable when anatomical peculiarities prevent a disintegrating or extracting tool from being brought into contact with the concretion. In addition, this method minimizes the detrimental effect of vibration upon the internal organs and nervous system of the patient.

In order to make the best use of the proposed method it is advisable to expose the ureteral walls to vibrations at frequencies ranging from 18 to 30 kHz.

Ultrasonic vibrations give rise to a stable spasmolytic effect which is conducive to a faster passage of a concretion from the ureter. Furthermore, ultrasonic waves die away more quickly than vibrations of sonic and lower frequencies, which practically excludes the danger of damaging the internal organs of the patient.

It is expedient to act upon the ureteral walls by ultrasonic vibrations with an amplitude varying over the range 10 to 20$\mu$ (micron).

It is preferable to subject the ureteral walls to ultrasonic vibrations in cycles, alternating vibrations and pauses, and maintaining a 1/10 ratio between the durations of vibratory action and a pause.

According to individual anatomical peculiarities, it is advantageous to maintain the duration of a pause equal to 5 s., when vibratory action takes 0.5 s., and 10 s., when the vibratory action takes 1 s.

It is preferable to maintain the total duration of ultrasonic vibratory action upon the ureteral walls within a single seance of treatment longer than 60 s. but shorter than 120 s.

This time is sufficient for stimulating effective peristaltic contractions of the ureter, whereas negative attendant factors, such as excessive heat generation or vibrations do not yet seriously affect the organism.

These and other objects and advantages of the present invention will become more apparent from the following detailed description of specific embodiments thereof, taken in conjunction with the accompanying drawings, wherein.

Figure 1:
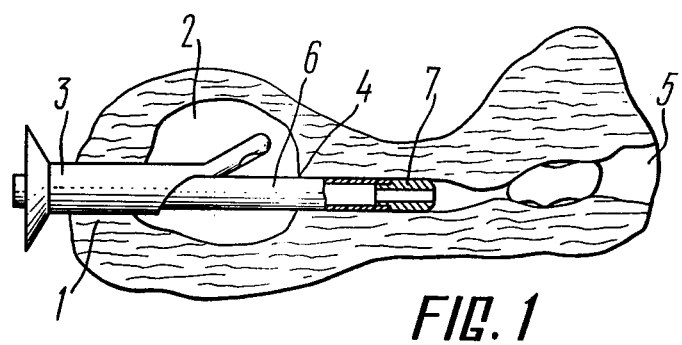
FIG. 1 shows the arrangement of a catheter and a cystoscope prepared for removing a concretion.

The proposed method of removing concretions from the ureter is carried out as follows. A 1% solution of diphenylhydramine hydrochloride (promedol) is administered to the patient. Then, a cystoscope 3 is introduced into the bladder 2 through the urethra 1. Under visual observation, a catheter 6 is introduced cystoscopically into the meatus 4 of the ureter 5 and pushed forward until its free tip 7 reaches the region of the ureter below the location of a concretion 8, as shown in FIG. 1.

Figure 2:
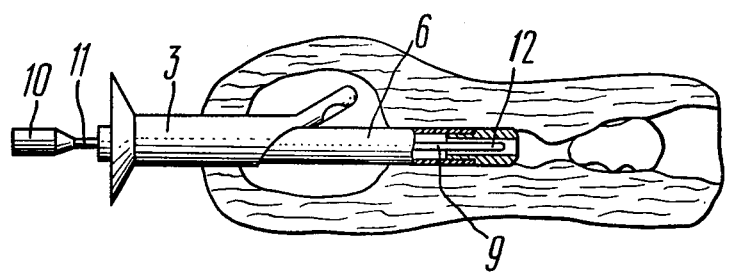
FIG. 2 shows the arrangement of a vibratory means acting upon the ureteral walls by vibrations, according to the invention.

Through the catheter 6, a vibratory means 9 is passed which may be any conventional means for ultrasonic disintegration of concretions, having an ultrasonic transducer 10 and a coupling element 11 with a working tool 12 at the end, (cf. U.S. Pat. No. 3,830,240). The vibratory means 9 is pushed forward until it reaches the tip 7 of the catheter 6 introduced into the ureter 5, without entering the ureter, as shown in FIG. 2. Then, the organism of the patient is subjected to vibratory action by the vibratory means 9 which, according to the invention, forces the walls of the ureter 5 below the location of the concretion 8 into vibration through the catheter 6, thereby stimulating persitaltic contractions. Note that vibrations of the organism tissue in the region adjoining the ureter die away rather rapidly and do not exert any adverse effect on the internal organs and the nervous system of the patient.

After completing a seance of vibratory action, the vibratory means 9 is withdrawn from the catheter 6.

Figure 3:
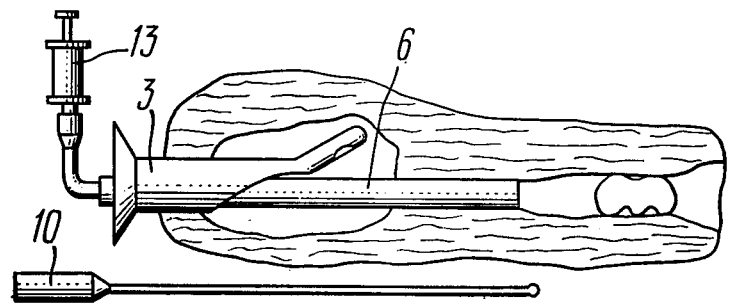
FIG. 3 shows the arrangement of a catheter and a vibratory means when peristaltic and anti-inflammatory preparations are injected into the ureter.

3 cu. cm of a glycerol solution and 3 cu. cm of a 2% solution of novocain (procaine hydrochloride) are injected by means of a syringe 13 through the catheter 6 into the region where the concretion 8 is logded, as illustrated in FIG. 3, to increase the spasmotic effect and provide for an anti-inflammatory effect.

Figure 4:
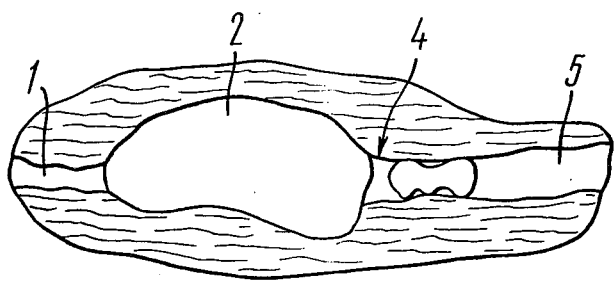
FIG. 4 shows the position of a concretion as it is being removed under the action of peristaltic contractions of the ureter.

The medical preparations having been administered into the ureter, the catheter 6 and the cystoscope 3 are withdrawn from the urinary tracts of the patient. Subsequently, the concretion 8 passes along the ureter under the action of the peristaltic contractions induced by vibrations, as shown in FIG. 4. The spasmolitic and anti-inflammatory preparations previously injected into the ureter, aid in moving the concretion and minimize damages to the internal ureteral wall by the moving concretion.

Figure 5:
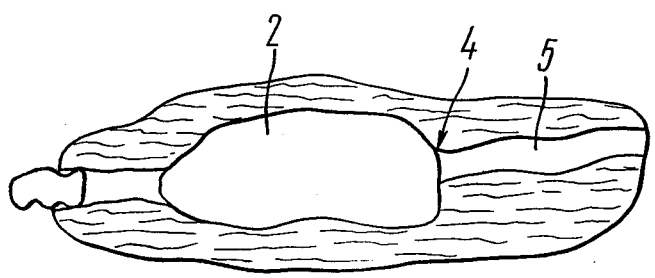
FIG. 5 shows the position of a concretion at the moment of its being removed from the ureter.

On the second to the sixth day, the concretion passes through the ureter, as shown in FIG. 5.

It is strongly recommended that the patient move as much as possible after the stage of vibratory actions is completed. As a rule, there is no need for him to stay in the hopsital longer than a day.

The frequency range of vibrations causing a spasmotic effect has been found fairly wide. However, the most preferable is an embodiment of the invention which provides for an ultrasonic vibratory action on the ureteral walls, as is illustrated below in examples.

EXAMPLE 1

After administering 1 cu. cm of a 1% solution of trimeperidine hydrochloride (promedol) and 1 cu. cm of a 1% solution of diphenylhydramine hydrochloride to the patient, the inner surface of the ureteral walls below the concretion were exposed to a vibratory action. According to individual features of an organism, the ultrasonic frequency of vibratory action was selected within the range from 18 to 30 kHz. The selection of a particular frequency was based on the patient's sensitivity to high-frequency ultrasonic vibrations. Practically all patients stand a vibration frequency of $22\pm1.5$ kHz fairly well. The amplitude of ultrasonic vibrations was in the range from 10 to 20 microns. The ureteral walls where subjected to ultrasonic vibrations cycle-by-cycle by vibratory action alternating with pauses. The ratio between the duration of each cycle of ultrasonic vibratory action and the length of each pause was maintained equal to 1/10. In particular, the duration of each cycle was maintained equal to 0.5 s., the length of each pause being equal to 5 s. The total duration of ultrasonic vibratory action upon the ureteral walls was equal to 120 s. After completion of the vibratory action, 3 cu. cm of a glycerol solution and 3 cu. cm of a 2% novocain solution were injected into the ureter. The concretion about 7 mm in size left the ureter on the second day. Examination of the patient having been subjected to vibratory action and subsequent medical observation of his state showed that the ultrasonic vibrations had not produced any adverse effects on his organism.

EXAMPLE 2

A concretion was removed from the ureter by the same manipulations as described above, under the same conditions, except for the length of pauses. In particular, the duration of each cycle of ultrasonic vibratory action was maintained equal to 1 s. and the length of a pause, equal to 10 s. The total duration of ultrasonic action was equal to 60 s. The concretion, lodged in the ureter for a long period of time, passed therefrom after two days during which the patient moved much and actively. The size of the concretion was 5 mm.

EXAMPLE 3

A concretion was removed from the ureter by the same manipulations as in example 1, and under the same conditions of ultrasonic vibratory action, except for the duration of the treatment seance. The total duration of ultrasonic action upon the ureteral walls was equal to 60 s. The concretion about 4 mm in size came out on the second day.

EXAMPLE 4

A concretion was removed from the ureter by the same manipulations as in example 1 and under the same conditions of ultrasonic action, except for the duration of vibratory action cycles, the length of pauses, and the total duration of the ultrasonic action. The duration of each cycle of ultrasonic action upon the ureteral walls was maintained equal to 1 s. and the length of each pause, equal to 10 s. The total duration of ultrasonic vibratory action was equal to 120 s. The concretion about 9 mm in size came out of the ureter on the 5 to 6th day. Throughout the following year, the patient was under continuous medical observation. No functional derangements in the activity of the ureter were noticed.

The method according to the invention has been approved at the Urology Section of the Kiev District Military Hospital No. 408. Out of 53 patients, a positive medical effect was observed on 41 patients. In the case of these 41 patients, concretions, lodged in the ureter for a long period of time, came out on the second or third day after the application of the above-described method. This method was used for internal treatment of patients whose anatomical peculiarities did not permit application of extractors as well as ultrasonic or electrohydraulic lithotriptors. In some cases, there were noticed signs of diseases of internal organs as well as peripheral nervous system. No detrimental effects upon the course of the disease were noted after the treatment according to the invention.

It is to be understood that the present invention, herein shown and described, is to be taken as preferred embodiments, and that various modifications thereof may be made within the spirit and scope of the invention as defined in the claims.

What we claim is:

1. Method of removing a concretion from a ureter containing a concretion, which comprises placing a vibratory means in the ureter cystoscopically through the urethra and the bladder, advancing said vibratory means through the ureter to the flexure thereof below and not in contact with the concretion, supplying power to said vibratory means inducing vibrations which act upon the inner surface of the ureteral walls and stimulate peristaltic contractions of the ureter, and withdrawing said vibratory means from the ureter, said stimulated peristaltic contractions being sufficient to cause said contained concretion to move through and out of the ureter, after said vibratory means has been withdrawn, without the concretion having been physically contacted by any instrument.

2. The method of claim 1, wherein the ultrasonic vibratory action upon the ureteral walls is effected with an ultrasonic frequency in the range of 18 to 30 kHz.

3. The method of claim 2, wherein the amplitude of the ultrasonic vibrations acting upon the ureteral wall varies within the range of 10 to 20 microns.

4. The method of claim 3, wherein said ultrasonic vibrations are interupted periodically by pauses in which no vibratory action occurs, the ratio between the duration of said ultrasonic vibrations and the duration of said pauses being 1:10.

5. The method of claim 4, wherein the duration of each cycle of ultrasonic vibratory action is equal to 0.5 second; the length of each pause being equal to 5 seconds.

6. The method of claim 4, wherein the duration of each cycle of ultrasonic vibratory action is equal to 1 second; the length of each pause being equal to 10 seconds.

7. The method of claim 4, wherein the total duration of ultrasonic vibratory action upon the ureteral walls in a seance of treatment is more than 60 seconds. but less than 120 seconds.

8. The method of claim 1, wherein spasmolytic and anti-inflammatory preparations are injected into the ureter after withdrawal of said vibratory means therefrom.

9. The method of claim 8, wherein a solution of glycerol and a 2% solution of novocain are used as said spasmolytic preparation, and wherein a solution of penicillin is used as said anti-inflammatory preparation.

10. The method of claim 9, wherein said spasmolytic preparation comprises 3 cu. cm of said novocain solution and 3 cu. cm of said glycerol solution.

* * * * *